United States Patent
Ben-Hur et al.

(10) Patent No.: US 6,541,229 B1
(45) Date of Patent: Apr. 1, 2003

(54) VITAMIN E AND DERIVATIVES THEREOF PREVENT POTASSIUM ION LEAKAGE AND OTHER TYPES OF DAMAGE IN RED CELLS THAT ARE VIRUS STERILIZED BY PHTHALOCYANINES AND LIGHT

(75) Inventors: Ehud Ben-Hur, New York, NY (US); Shanti Rywkin, Brooklyn, NY (US); Bernard Horowitz, New Rochelle, NY (US)

(73) Assignee: New York Blood Center, Inc., New York, NY (US)

( * ) Notice: Subject to any disclaimer, the term of this patent is extended or adjusted under 35 U.S.C. 154(b) by 0 days.

(21) Appl. No.: 09/418,802

(22) Filed: Oct. 15, 1999

Related U.S. Application Data

(63) Continuation of application No. 08/340,557, filed on Nov. 16, 1994, now Pat. No. 6,077,659, which is a continuation-in-part of application No. 08/191,907, filed on Feb. 4, 1994, now abandoned, which is a continuation-in-part of application No. 08/069,235, filed on May 28, 1993, now abandoned, which is a continuation-in-part of application No. 08/031,787, filed on Mar. 15, 1993, now abandoned, which is a division of application No. 07/706,919, filed on May 29, 1991, now Pat. No. 5,232,844, which is a continuation-in-part of application No. 07/524,208, filed on May 15, 1990, now Pat. No. 5,120,649.

(51) Int. Cl.$^7$ .......................... C12N 13/00; A01N 1/02
(52) U.S. Cl. ...................................... 435/173.4; 435/2
(58) Field of Search ................... 435/2, 173.4

(56) References Cited

U.S. PATENT DOCUMENTS 4,847,071 A  *  7/1989 Bissett et al.

OTHER PUBLICATIONS

Chiu et al., "Peroxidation, Vitamin E, and Sickle–Cell Anemia", Annals Of The New York Academy Of Sciences, (1982) vol. 393, 323–335.*

Wolters et al., "Membrane Radiosensitivity Of Fatty–Acid Supplemented Fibroblasts As Assayed By The Loss Of Intracellular Potassium", Int J Radiat Biol Relat Stud Phys Chem Med, (1985) 48 (6), 963–974.*

* cited by examiner

*Primary Examiner*—Jon P. Weber
(74) *Attorney, Agent, or Firm*—Amster, Rothstein & Ebenstein

(57) ABSTRACT

Disclosed is an improved process for irradiating cell-containing compositions, especially, red cell-containing compositions, wherein vitamin E or a derivative thereof is added to the cell-containing composition prior to, during or after such irradiation. Addition of vitamin E or a derivative thereof is protective of cells in such compositions, but not of virus. Cells irradiated using the inventive process show a reduced leakage of $K^+$ from cells and also a reduced loss of negative charges from the cell membrane compared to cells subjected to the similar process wherein vitamin E or a derivative thereof are not used. In addition, red blood cells sterilized by this process are better preserved during storage and their life-time in the circulation in vivo is greatly enhanced.

4 Claims, 4 Drawing Sheets

VITAMIN E AND DERIVATIVES THEREOF PREVENT POTASSIUM ION LEAKAGE AND OTHER TYPES OF DAMAGE IN RED CELLS THAT ARE VIRUS STERILIZED BY PHTHALOCYANINES AND LIGHT

This application is a continuation of U.S. Ser. No. 08/340,557, filed Nov. 16, 1994, now U.S. Pat. No. 6,077,659, which is, in turn, a continuation-in-part of U.S. Ser. No. 08/191,907, filed Feb. 4, 1994, now abandoned; which is, in turn, a continuation-in-part of U.S. Ser. No. 08/069,235, filed May 28, 1993, now abandoned; which is, in turn, a continuation-in-part of U.S. Ser. No. 08/031,787, filed Mar. 15, 1993; which is, in turn, a divisional of U.S. Ser. No. 07/706,919, filed May 29, 1991, now U.S. Pat. No. 5,232,844; which is, in turn, a continuation-in-part of U.S. Ser. No. 07/524,208, filed May 15, 1990, now U.S. Pat. No. 5,120,649.

BACKGROUND OF THE INVENTION

1. Field of the Invention

The present invention concerns an improved process for rendering a cell-containing composition substantially free of enveloped and non-enveloped viruses contained therein without substantial disruption or inactivation of cells contained therein and without significant loss of labile proteins or other valuable biological components also contained therein.

2. Description of the Related Art

Viral inactivation of cell-containing composition by treatment with irradiation, e.g., UV or visible light, a photosensitizer compound and, optionally, one or more quencher compounds has been described in the applications and patents mentioned above, the entire disclosures of which are hereby incorporated by reference. Such treatments are known to cause $K^+$ leakage from red cells. See, e.g., J. van Steveninck et al., 1985, "The influence of cupric ions on porphyrin-induced photodynamic membrane damage in human red blood cells", *Biochim. Biophys. Acta.*, 821: 1–7.

Irradiation is used in other contexts involving cell-containing compositions for example, ionizing radiation, e.g., γ-irradiation or X-irradiation, to prevent graft-versus host disease in immunodeficient patients. For this particular purpose, collected red cells increasingly are being stored for variable periods in transfusion service inventories following irradiation. Other reports of elevated $K^+$ in irradiated, stored RBC, have recently surfaced. See, for example, Elaine K. Jeter et al., 1991, "Effects of irradiation on red cells stored in CPDA-1 and CPD-ADSOL (AS-1)", *Ann. Clin. Lab. Sci.*, 21: 177–186; and A. M. Ramirez et al., 1987, "High potassium levels in stored irradiated blood", *Transfusion*, 27: 444–445. For blood centers offering red cell irradiation, prolonged storage following irradiation may expose selected patient populations to a significant $K^+$ load following transfusion.

It also is known that morphological deformations of erythrocytes are induced by hematoporphyrin- a photosensitizer compound- and light. See, for example, Bruria Lev et al., 1993, "Morphological Deformations of Erythrocytes Induced by Hematoporphyrin and Light", *Lasers in the Life Sciences*, 5: 219–230. Specifically, hematoporphyrin-bound cells displayed a marked reduction in membranal negative-charges and sialic acid residues on their cell membranes.

SUMMARY OF THE INVENTION

We have found that photodynamic treatment of cell-containing compositions, particularly, red cells, for virus sterilization causes $K^+$ leakage during storage prior to transfusion and loss of negative charges from the cell membrane. We have also found that these effects following photodynamic treatment for viral inactivation are even more pronounced than that observed following ionizing irradiation for the purposes of preventing graft-versus-host disease.

The leakage of $K^+$ from cells, e.g., red cells, may limit their usefulness, e.g., in transfusions. Moreover, loss of negative charges from the cell membrane reduces the life span of the cell, i.e., the life-time in the circulation in the case of a red cell.

Accordingly, it was the main object of the present invention to provide a means by which cell-containing compositions could be irradiated for the purpose of viral sterilization without inducing pronounced leakage of $K^+$ from cells or loss of negative charges from the cell membrane.

It was also an object of the present invention to provide a virus sterilization protocol more compatible for transfusion purposes.

It was another object of the present invention to provide a means by which a reduction could be effected in both $K^+$ leakage and the loss of cell membrane surface negative charges.

It was a further object of the present invention to provide a protocol for irradiation of blood in connection with the prevention of graft-versus-host disease by which processed blood more compatible for transfusion could be obtained.

These and other objects are met with the present invention which provides for a process for inactivating virus contained in a cell-containing composition without damaging desirable biological proteins contained in said cell-containing composition, said process comprising subjecting said cell-containing composition to a photosensitizer compound, light and a vitamin, e.g., vitamin E, or a derivative thereof, e.g., a derivative of vitamin E, for a period of time sufficient to substantially inactivate virus contained in said cell-containing composition.

We have discovered that vitamin E and its derivatives have the surprising ability to materially reduce leakage of $K^+$ from cells or loss of negative charges from the cell membrane.

The invention also relates to a process for preventing graft-versus-host disease comprising ionizing irradiation of red cells, wherein the improvement comprises incubating said red cells with vitamin E or a derivative thereof before, during and after said ionizing irradiation.

The invention further relates to a process for inactivating virus in a cell-containing composition by treating the cell-containing composition with a photodynamic compound under light, wherein the improvement comprises said treatment is carried out in the presence of vitamin E or a derivative thereof.

BRIEF DESCRIPTION OF THE DRAWINGS

The invention will now be described in further detail with reference to the drawings, wherein.

DETAILED DESCRIPTION OF THE INVENTION

Figure 1:
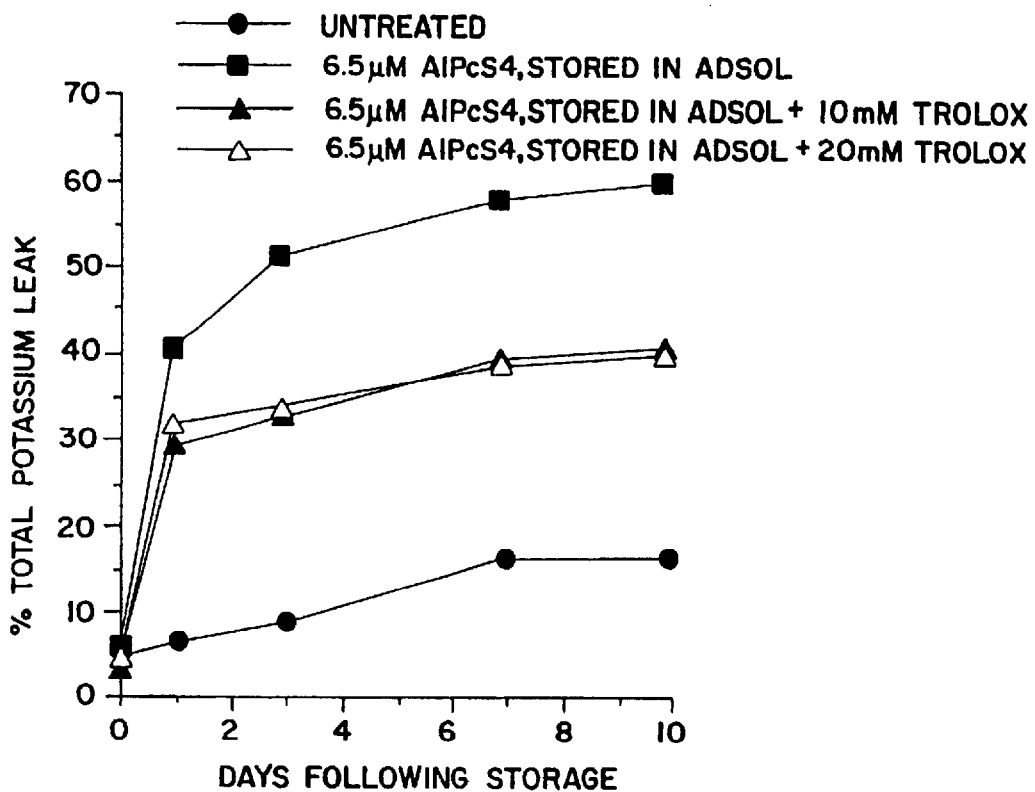
FIG. 1 is a graph demonstrating the effects of varying concentrations of Trolox™ on potassium ion ($K^+$) leakage after irradiation of red blood cells (RBC) with aluminum phthalocyanine tetrasulfonate ($AlPcS_4$)

The inventive methods are particularly applicable to the processing of blood, which is made up of solids (cells, i.e., erythrocytes, leukocytes, and platelets) and liquid (plasma). The cells are transfused in the treatment of anemia, clotting disorders, infections, etc. In addition, the cells contain potentially valuable substances such as hemoglobin, and they can be induced to make other potentially valuable substances such as interferon, growth factors, and other biological modifiers.

The term "cell-containing composition" as used herein is not to be construed to include any living organism. The inventive methods are intended to be conductive ex vivo. Non-limiting examples of such "cell-containing compositions" are whole blood, fetal cord blood, red blood cell concentrates, platelet concentrates, platelet extracts, leukocyte concentrates, semen, ascites fluid, milk, lymphatic fluid, progenitor cells, bone, bone marrow, stems cells, hybridoma cell lines and products derived from any of the above. In a particularly preferred embodiment, the cell-containing composition is blood, particularly blood intended for transfusion.

Cell-containing compositions to be treated according to the invention have up to 1×10$^{10}$ cells/ml, preferably ≧1×10$^8$ cells/ml, very preferably ≧1×10$^9$ cells/ml, and most preferably ≧2–6×10$^9$ cells/ml. Furthermore, cell-containing compositions to be treated according to the invention generally have up to 60 mg/ml, preferably >4 mg/ml protein, more preferably >25 mg/ml protein, and most preferably 50 to 60 mg/ml protein, (unwashed cells).

The viral inactivation with the photosensitizer compound and light is carried out on the cell-containing composition in the customary manner. Details on the application of irradiation and a photosensitizer compound to such cell-containing compositions are described in the abovementioned patents and applications.

The term "irradiation" is to be construed broadly to include any form of radiation conventionally used to inactivate cells, e.g., white blood cells, or viruses, or parasites or other pathogenic organisms, e.g., *toxoplasma gondii, trypanosoma cruzi, plasmodium malarie*, or *babesia microti*, either alone or combined with some other agent or condition. Non-limiting examples of irradiation include UV (UVA, i.e., UVA1, UVA2 or a combination of both, UVB and UVC), gamma-irradiation, x-rays and visible light.

Details on the application of radiation to effect virus inactivation are well known to those skilled in the art.

Typical radiation fluence ranges for the inventive process are 5–100 J/cm$^2$ (preferably 50–100 J/cm$^2$) for UVA; 0.02–2 J/cm$^2$ (preferably 0.05–2 J/cm$^2$) for UVC, and 1–40 kGy for τ irradiation.

The photosensitizer compound is selected from the group comprising phthalocyanines, purpurins, and other molecules which resemble the porphyrins in structure, as well as photoactive compounds excited by ultraviolet light (e.g., psoralen, 8-methoxypsoralen, 4'-aminomethyl-4,5',8-trimethylpsoralen, bergapten and angelicin), dyes which absorb light in the visible spectrum (e.g., hypericin, methylene blue, eosin, fluoresceins and flavins), and dyes which absorb X-irradiation (e.g., brominated psoralen, brominated hematoporphyrin and iodinated phthalocyanine). The use of such photosensitizer compounds is readily apparent to those skilled in the art and is preferably substantially as described in U.S. Pat. No. 5,120,649 and U.S. Ser. No. 07/706,919, filed May 29, 1991, which have been mentioned previously.

Preferably, the photosensitizer compound is a phthalocyanine (Pc), i.e., porphyrin-like synthetic dyes with an intense absorption band at 650–700 nm. Our previous studies have shown that virucidal action could be maximal and RBC damage minimal by careful selection of the phthalocyanine derivative (see E. Ben-Hur et al., *Photochem. Photobiol.,* 58:351 (1993); Z. Smetana et al., *Photochem. Photobiol.,* 22:37 (1994); and S. Rywkin et al., *Photochem. Photobiol.,* 60:165–170 (1994)), by increasing the rate at which light was delivered (fluence rate) (see E. Ben-Hur et al., *Photochem. Photobiol.,* 61:000—000 in press (1995)) and by adding quenchers of type 1 photodynamic reactions (free radicals) such as mannitol prior to irradiation (see S. Rywkin et al., *Photochem. Photobiol.,* 56:463 (1992)). The enhanced specificity in the latter was interpreted to be due to type II (singlet oxygen) being the main mediator of virus kill while both types I and II reactions contribute to RBC damage. As a consequence of these investigations we have identified new silicon phthalocyanine (Pc5) with enhanced virucidal action (see S. Rywkin et al., *Photochem. Photobiol.,* 60:165–170 (1994)); however, it also caused more RBC damage than our previously employed aluminum phthalocyanine tetrasulfonate (AlPcS$_4$) (see R. Rywkin et al., Id.). As a result, more effective type I quenchers than mannitol were sought. One such antioxidant is vitamin E, which inhibits AlPcS$_4$-induced photohemolysis of RBC. For practical purposes, we chose to study a water-soluble derivative of vitamin E, Trolox™ C, in which the phytol chain of α-tocopherol is replaced by carboxyl. Trolox™ is a powerful quencher of protein radical reactions. See C. Giulivi et al., *Arch. Biochem. Biophys.* 303:152 (1993). Although tocopherols in general are efficient physical and chemical quenchers of singlet oxygen, the results reported below surprisingly show that while Trolox protects RBC against photodynamic damage induced by phthalocyanines, it does not protect against virus inactivation.

The vitamin E or the derivative thereof is ordinarily added to the cell-containing composition before irradiation. The vitamin E or the derivative thereof is used in an effective quenching amount, which is readily apparent to those skilled in the art, but is especially beneficial when used in an amount of from 2 to 10 mM.

The derivatives of vitamin E are any that are known to those of ordinary skill in the art, including the following non-limiting list: vitamin E (α-tocopherol), α-tocopherol succinate and α-tocopherol phosphate. However, we have found that the best results are obtained when the derivative is Trolox™ (6-hydroxy-2,5,7,8-tetramethylchroman-2-carboxylic acid). The very best results are achieved by subjecting the cell-containing composition to a combination of a phthalocyanine, especially, AlPcS$_4$, Pc4 or Pc5, red light and Trolox™. Another preferred embodiment contemplates the use of vitamin E itself.

Vitamin E and derivatives thereof are quenchers of type I primarily. It may prove advantageous to couple the treatment with vitamin E with other conventional quencher compounds in the customary quenching amounts, e.g., unsaturated fatty acids, reduced sugars, cholesterol, indole derivatives, and the like, azides, such as sodium azide, tryptophan, polyhydric alcohols such as glycerol and mannitol, thiols such as glutathione, superoxide dismutase, flavonoids such as quercetin and rutin, amino acids, DABCO, other vitamins and the like. In the best embodiments, when phthalocyanines are used as sensitizers, the quenchers are chosen so that type I photodynamic reactions are quenched. This is because under these conditions virus inactivation occurs by type II reaction while cell damage is mediated by both type I and type II reactions. The result is that a broader range of virus kill is achieved and without sacrificing intact cell functionality or structure.

The inventive viral inactivation process is ordinarily carried out over a temperature range of 0–42° C., preferably 20–37° C. and most preferably 20–25° C. This process also is typically carried out at pH 6.5–8, most preferably 7.2–7.6. Samples are ordinarily subjected to this process for the period of time that it necessary to inactivate substantially all virus contained in the cell-containing composition and this period of time is usually less than 24 hours, preferably less than 4 hours for, γ, X-irradiation or visible light. Samples can also be treated while frozen in the case of ionizing radiation.

Using this viral inactivation process, it is possible to inactivate both lipid coated, human pathogenic viruses and non-enveloped viruses, as well as other pathogens. Non-limiting examples of such viruses are set forth in the abovementioned patents and applications. Using this viral inactivation process, it is possible to inactivate at least $10^4$, preferably $10^6$, infectious units of such virus, parasite or other pathogen while at the same time cells in the composition that is treated are protected from substantial disruption or activation.

The cell-containing compositions treated according to the invention, while initially containing ≧1000 infectious units of virus/L, after the virus has been inactivated and treatment according to the invention has been conducted, have a retention of intact cell functionality and structure of greater than 70%, preferably greater than 80% and most preferably greater than 95%. Moreover, the cells therein are characterized by a reduced leakage of $K^+$ from cells and loss of negative charges from the cell membrane compared to cells subjected to the similar process wherein vitamin E or a derivative thereof are not used. Particularly, after prolonged storage, cells subjected to the inventive process showed a marked reduction in the leakage of $K^+$ from such cells, and reduced hemolysis.

A similar reduction in the leakage of $K^+$ from cells can be effected by adding vitamin E or a derivative thereof to compositions containing cells that are prone to $K^+$ leakage either normally or after harsh treatment, e.g., irradiation. For example, the $K^+$ leakage observed after irradiation of blood to prevent graft-versus-host disease also can be substantially reduced by adding vitamin E or a derivative thereof to such blood prior to irradiation. The vitamin E or derivative thereof is added in the amounts previously mentioned. In a particularly preferred embodiment, Trolox™ is added.

The invention will now be further described with reference to the following non-limiting examples:

EXAMPLE 1

RBC were treated under standard conditions for complete virus inactivation using the photosensitizer AlPcS$_4$ and red light (i.e., 30 min of red light exposure at a fluence rate of 25 mW/cm$^2$ such that total light exposure was 45 J/cm$^2$). The results are shown in FIG. 1. At various times after light exposure (days on the abscissa) the % $K^+$ leaked from the cells was measured in the extracellular medium (% $K^+$ on the ordinate). The curves show the results under various conditions:

2. Untreated, control RBC;
2. RBC treated under standard condition (6.5 μM AlPcS$_4$+4 mM glutathione);
3. Same treatment as in 2., but with the addition of 10 mM Trolox™; and
4. Same treatment as in 2., but with the addition of 20 mM Trolox™.

EXAMPLE 2

RBC were treated for virus inactivation with the photosensitizer Pc 5 and various intervals of exposure to red light. Complete virus kill was achieved after 30 min irradiation. After light exposure, the percentage of negative charges on the cell surface was measured using binding of the cells to poly-L-lysine (PLL). The extent of binding to this positively charged polymer is directly related to the number of negative charges. The results are expressed as a percentage of untreated control cells. The curves show the results under various conditions:

2. RBC treated with 2 μM Pc 5;
2. RBC treated with 2 μM Pc 5+0.1 mM Trolox™;
3. RBC treated with 2 μM Pc 5+0.5 mM Trolox™;
4. RBC treated with 2 μM Pc 5+2.5 mM Trolox ™; and
5. RBC treated with 2 μM Pc 5+10 mM Trolox™.

The foregoing examples prove that vitamin E and derivatives thereof, e.g., Trolox™, protect red cells under conditions necessary for viral inactivation. Further proof of the advantages of the present invention should be apparent from the following example.

EXAMPLE 3

Rabbit RBC were treated with Pc 4 and 35 min of red light (52.5 J/cm$^2$) to obtain complete virus inactivation in the presence or absence of 5 mM Trolox. The cells were then labeled with radioactive Cr ($^{51}$Cr) and infused back into autologous rabbits. The life-time ($T_{1/2}$) of RBC in the circulation was determined by bleeding the rabbits at time intervals and measuring the radioactivity associated with the RBC. The results obtained for untreated RBC were $T_{1/2}$=8.5 days; for RBC treated without Trolox, $T_{1/2}$=5 hours; and for RBC treated with Trolox, $T_{1/2}$=2.5 days.

This example proves that the protection of RBC by Trolox is manifested not only in vitro but also in vivo.

MATERIALS AND METHODS

RBCC:

While blood, obtained from the New York Blood Center, was centrifuged at 1800 rpm for 20 min and the plasma and white blood cells removed. The RBCC (70% hematocrit) was diluted 1:1 with phosphate buffered saline (PBS) for treatment.

Light Exposure:

Prior to irradiation, phthalocyanines were added to the RBC with or without Trolox™. After 30 min at room temperature, 3 ml samples in polystyrene tubes were irradiated with red light from a 300 W Xenon Lamp (Oriel Corp., Stratford, Conn.) equipped with a cut-off filter transmitting at $\lambda > 600$ nm. The fluence rate incident to the samples was 25 mW/cm$^2$, measured with a photometer (model IL 1350, International Light, Newburyport, Mass.). During irradiation the samples were rotated and rolled on a hematology mixer to obtain even exposure. Sample temperature did not exceed 25° C.

Chemicals:

Aluminum phthalocyanine tetrasulfonate (AlPcS$_4$) was purchased from Porphyrin Products (Logan, Utah). The cationic silicon phthalocyanine HOSiPcOSi(CH$_3$)$_2$ -(CH$_2$)$_3$ N$^+$(CH$_3$)$_3$I (Pc 5) and its neutral analog Pc 4 were kindly supplied by Prof. M. E. Kenney. (N. L. Oleinick et al., *Photochem. Photobiol.*, 57:242 (1993))

Phthalocyanines were stored as 1 mM stock solutions in either PBS (AlPcS$_4$) or dimethyl sulfoxide (Pc 4 and Pc 5) at −20° C. Trolox™ was obtained from Aldrich and stored as 0.1 M aqueous solution at 4° C.

RBC Binding to Poly-L-Lysine:

The reduction of RBC negative surface charges as a result of photosensitization was assayed by measuring RBC binding to poly-L-lysine (PLL). See, S. Rywkin et al., *Photochem. Photobiol.*, 60:165–170 (1994). Briefly, following treatment, RBC were diluted in PBS to a concentration of 5×10$^6$ cells/ml. One ml of cell suspension was added into a 35 mm Petri dish, precoated with PLL at a concentration of 1 mg/ml H$_2$O for 1 hr, and incubated for 1 hr at room temperature. The dishes were then rinsed with PBS to remove nonbound cells, and the adsorbed cells were lysed with 2 ml distilled water. The absorbance of the lysate at 415 nm was used to quantitate the hemoglobin released from the bound cells. Results (average of triplicates per datum point) were calculated as percentage of untreated control. Standard errors were 5–10% and are not shown for clarity.

RBC Hemolysis During Storage:

The RBC to be stored following treatment were washed 2 times in PBS, suspended 1:1 in ADSOL (adenine solution) and 3 ml aliquots stored at 5° C. in Vacutainer glass tubes. The extent of hemolysis was determined by comparing the hemoglobin released to the total hemoglobin. Total hemoglobin was determined using the Drabkin reagent (Sigma Procedure #525) and absorption at 540 nm was used to calculate the amount of hemoglobin released in the supernatant. Measurements were done in triplicate.

K$^+$ Leakage During Storage

RBC were stored after treatment as described above for the hemolysis assay. The amount of K$^+$ in the supernatant was assayed with a K$^+$ electrode (Model 93–19, Orion Research, Inc., Boston, Mass.) in conjunction with ion analyzer (Model EA 940, Orion). The mV readings were converted into mM K$^+$ using a standard curve. Total K$^+$ was assayed after lysis of RBC in distilled water and the results are expressed as percentage of K$^+$ leaked.

Assay of Vesicular Stomatitis Virus (VSV):

VSV infectivity was assayed as described previously. See B. Horowitz et al., *Transfusion*, 31:102 (1991). Briefly, VSV was added to the RBC suspension to a final titer of approximately 10$^6$ infectious units (ID$_{50}$) per ml. After 30 min in the dark together with Pc 4, Pc 5 or AlPcS$_4$ with or without Trolox™ the samples were irradiated and the suspension diluted 1:10 with Dulbecco's modified Eagle's medium containing 5% fetal calf serum and centrifuged to remove RBC. The supernatants were sterile filtered by passing through 0.22 $\mu$m filters (Millipore) and stored frozen at −80° C. For assay, the samples were 10-fold serially diluted, inoculated into A549 cell cultures in 96-well microtiter plates and incubated at 37° C. in a CO$_2$ incubator for 72 hr. Cellular cytopathology was then scored in eight well replicates for each dilution and virus titer quantitated by the Spearman-Karber method. See C. Spearman, *Br. J. Psychol.*, 2:227 (1908). Standard errors of the data points were 0.5 log$_{10}$ and are not shown for clarity. Experiments were repeated twice and the differences were not statistically significant at all light fluences.

Flash Photolysis:

The transient absorption spectra and decay kinetics of AlPcS$_4$ with or without Trolox™ were recorded using a laser flash photolysis system. The system consisted of an N$_2$-laser as an excitation source (Everett Research Laboratory, 10 ns pulse duration, energy 0.2 nJ/pulse and 8×2 mm beam) and a pulsed high pressure 100 W xenon arc lamp in cross-section arrangements. The kinetic curves were averaged over 2000 laser pulses by a Tetronix TDS 620 oscilloscope coupled to an IBM 386 microcomputer.

Figure 2:
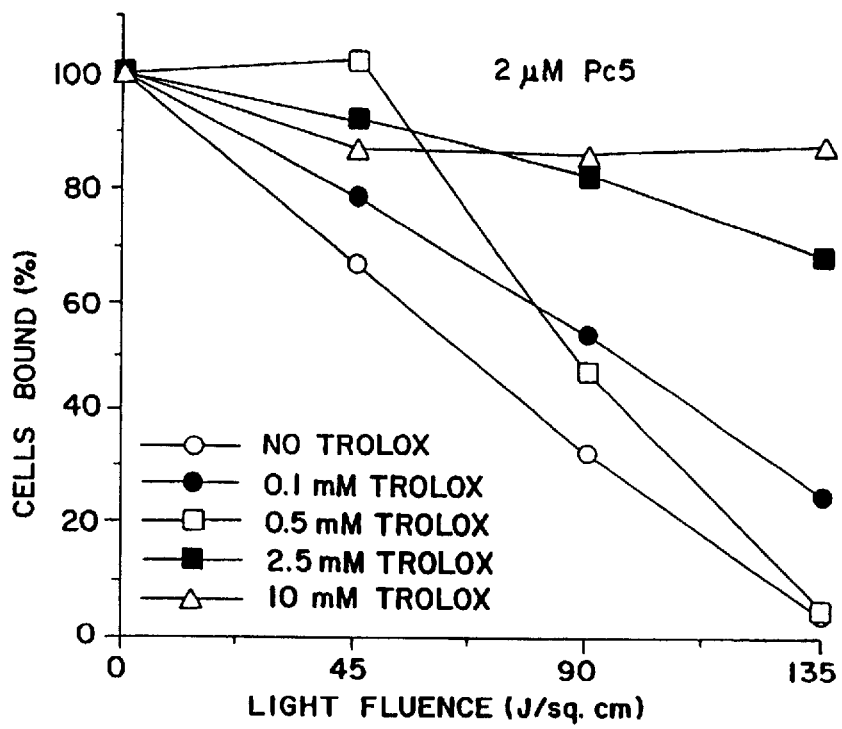
FIG. 2 is a graph demonstrating the effect of Trolox™ on RBC binding to PLL Red cell concentrates (RBCC) were exposed to graded light doses in the presence of 2 μM Pc 5 and various concentrations of Trolox™, an indicated.
Figure 3:
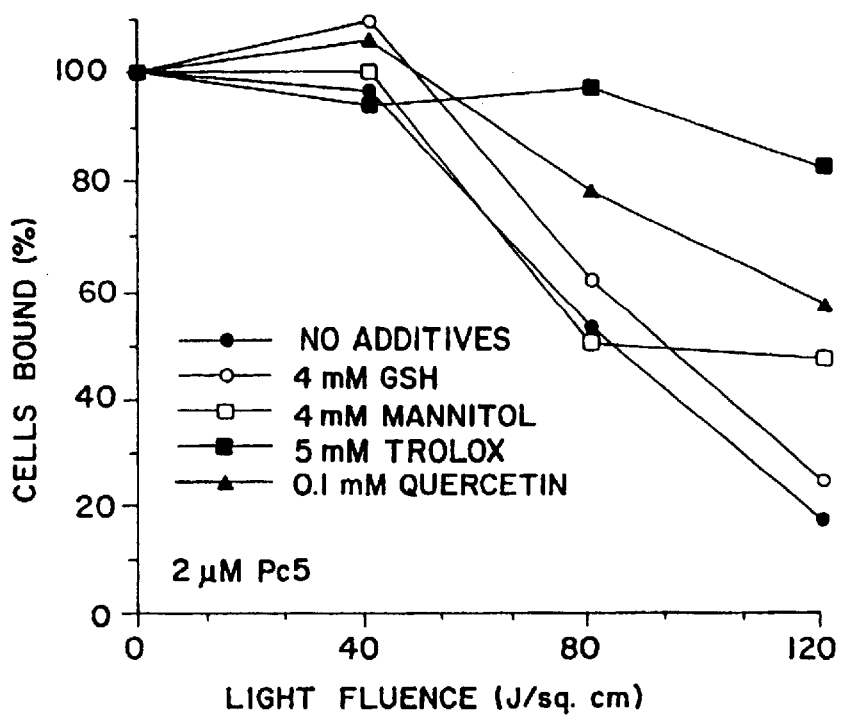
FIG. 3 is a graph demonstrating the effect of quenchers on RBC binding to PLL.
Figure 4:
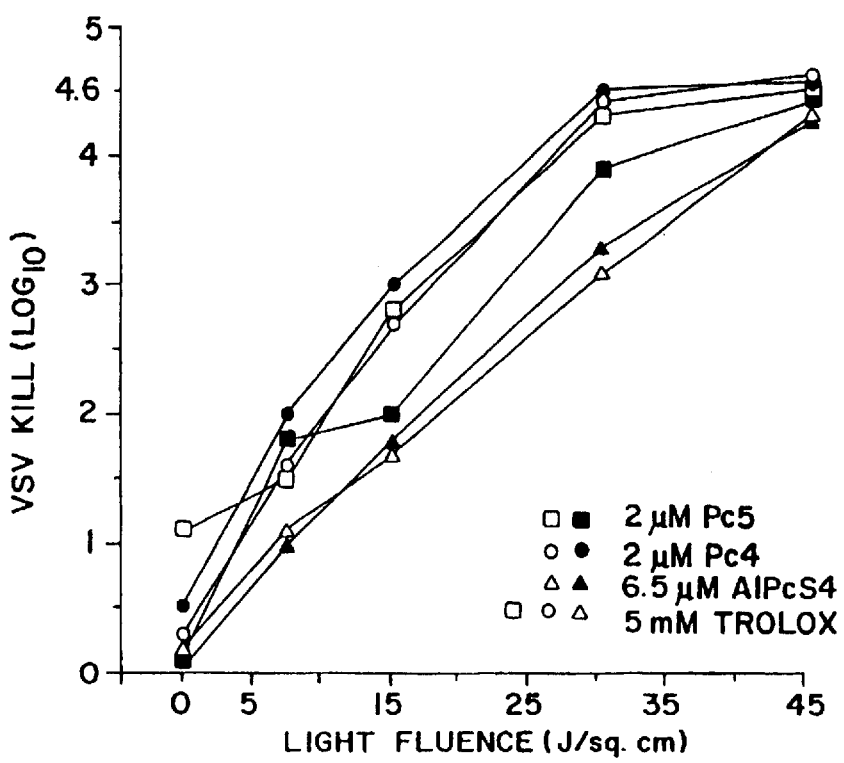
FIG. 4 is a graph demonstrating the effect of Trolox™ on VSV inactivation. RBCC were spiked with VSV and exposed to graded light doses in the presence of 2 μM Pc4, 2 μM Pc5 or 6.5 μM AlPcS$_4$, with or without 5 mM Trolox™, as indicated.

Results:

FIG. 2 shows the concentration dependence of the protection by Trolox™ against reduction in RBC negative surface charges. In the absence of Trolox™ exposure to red light in the presence of 2 $\mu$m Pc 5 caused a progressive reduction in RBC negative surface charges. The presence of Trolox™ during irradiation prevented this reduction, with a maximal protection achieved at 2.5–10 mM Trolox™. Of the various quenchers we have used in the past to protect against photodynamic damage to RBC, Trolox™ appears to be the most effective in inhibiting reduction of RBC negative surface charges when the quenchers were used at a concentration that affords close to maximal protection using other assays for RBC damage (FIG. 3). Quercetin, which can protect RBC against phthalocyanine-induced photohemolysis at the $\mu$m range, also protects against VSV inactivation. See E. Ben-Hur et al., *Photochem. Photobiol.*, 58:351 (1993); E. Ben-Hur et al., *Photochem. Photobiol.*, 58:984 (1993): and H. Margolis-Nunno et al., *Transfusion*, 34: (in press) (1994). Unlike quercetin, the kinetics of VSV inactivation as a function of light exposure in the presence of Pc 4, Pc 5 and AlPcS$_4$ were not significantly different when 5 mM Trolox™ was present during irradiation (FIG. 4).

Figure 5:
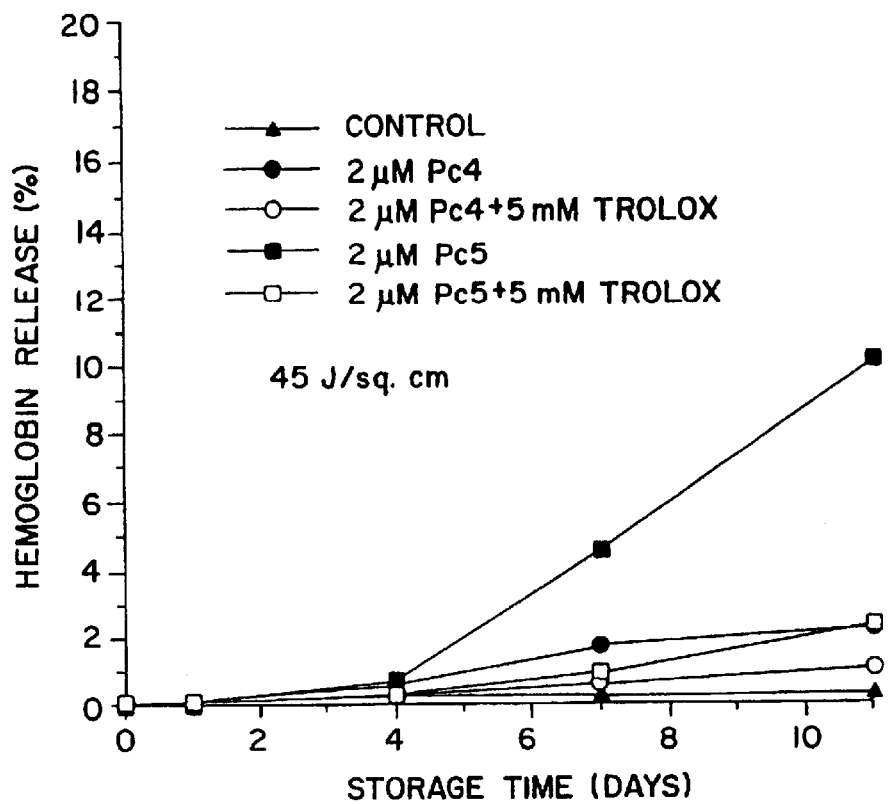
FIG. 5 is a graph demonstrating RBC hemolyis during storage. RBCC were exposed to ~45 J/cm$^2$ of red light in the presence of 2 μM Pc 5 or Pc 4 with or without Trolox™ at a concentration of 5 mM, as indicated.

The ability of Trolox™ to prevent RBC hemolysis during storage after treatment is shown in FIG. 5. Clearly, Pc 5 photosensitization caused more RBC damage than Pc 4. Trolox™ reduced the damage leading to hemolysis. In the case of Pc 4 elimination of the photodynamic damage was almost complete.

Figure 6:
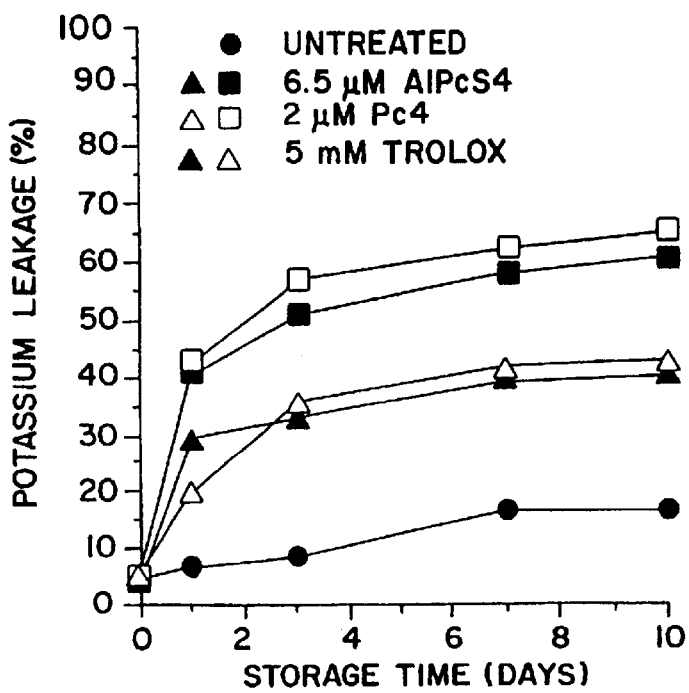
FIG. 6 is a graph demonstrating the effect of Trolox™ on K$^+$ leakage. RBCC were exposed to 45 J/cm$^2$ of red light in the presence of 2 μM Pc 4 or 6.5 μM AlPcS$_4$ with or without 5 mM Trolox™, as indicated. Leakage of K$^+$ out of RBC was assayed during storage after treatment.

K$^+$ leakage occurs after photodynamic treatment with many photosensitizers in various biological systems. See TMAR Dubbelman et al., "Photodynamic therapy: membrane and enzyme photobiology". In: Henderson B W, Dougherty T J, eds. *Photodynamic therapy: Basic principles and clinical applications*. New York: Marcel Dekker, 1992: pp. 37–46. As shown in FIG. 6 K$^+$ leakage occurs after a virucidal treatment with Pc 4 and AlPcS$_4$. The latter causes less RBC damage using other assays. See, B. Horowitz et al., *Transfusion*, 31:102 (1991); E. Ben-Hur et al., *Photochem. Photobiol.*, 58:351 (1993); and S. Rywkin et al., *Photochem. Photobiol.*, 60:165–170 (1994). The presence of Trolox™ during irradiation reduced the K$^+$ leakage by about 50%, when compared to control, untreated RBC. The results obtained with Pc 5 were essentially the same as with Pc 4 (not shown)

Figure 7:
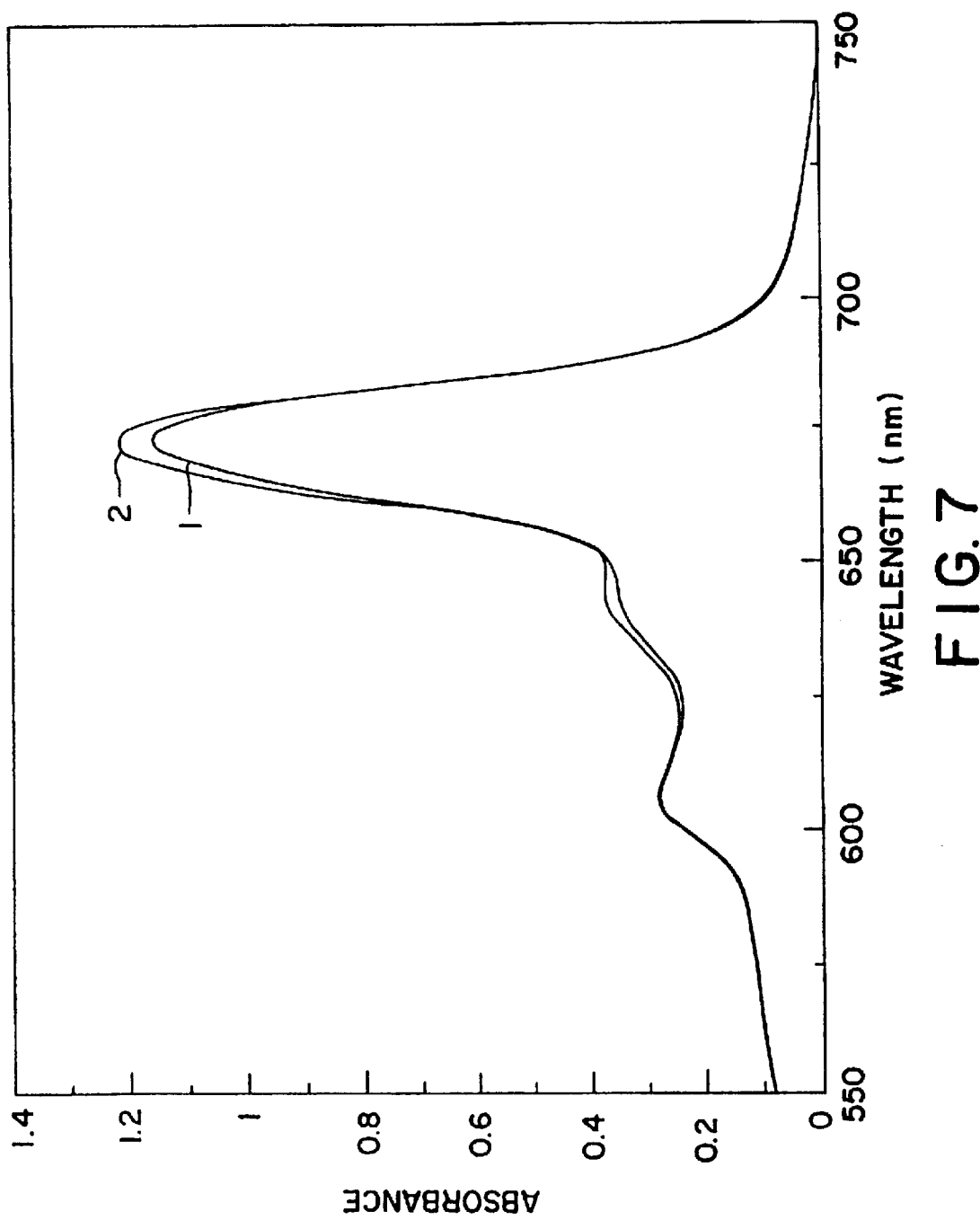
FIG. 7 is a graph demonstrating the absorption spectra of 10 μM AlPcS$_4$ in PBS in the presence of 2.5 mM Trolox™ (1) and in its absence (2). The curves for in-between concentrations have been deleted for clarity.

To gain further insight into the mechanism by which Trolox™ exerts its protective effect we studied its interaction AlPcS$_4$ in an aqueous solution. FIG. 7 shows that there is an association of the dye with Trolox™ as reflected by a small red shift of the Q absorption bands (671 to 672 nm and 605 to 606 nm) accompanied by a slight decrease in absorbance. The absorption spectrum plots of AlPcS$_4$ solutions in PBS containing increasing amounts of Trolox™ intersect at several isosbestic points (684,653,610,595 nm), which indicate that only one type of spectroscopically distinguishable ground-state complex Trolox™-AlPcS$_4$ is formed. The absorption changes are too small for calculation of a reliable ground-state association constant. The quenching rate of AlPcS$_4$ triplet state by Trolox™ was determined by flash photolysis as $8.8 \times 10^6$ $M^1s^1$. Unfortunately, similar studies could not be carried out in RBCC because of light scatter.

Collectively, the foregoing results demonstrate the ability of Trolox™ to protect RBC from photodynamic damage induced by phthalocyanines and red light as measured by PLL binding, hemoglobin release, K$^+$ leakage and circulatory survival in rabbits. Under the same conditions there is no protection by Trolox™ against viral inactivation. This latter result was somewhat unexpected since tocopherols can scavenge reactive oxygen species produced by both type I and type II photodynamic reactions. Selective protection of RBC and not of virus kill by phthalocyanines was previously obtained only with quenchers of type I reactions. See S. Rywkin et al., *Photochem. Photobiol.* 56:463 (1992).

It is interesting that in simple aqueous salt solution, our results indicate that Trolox™ can form a ground-state complex with phthalocyanines and quench their excited triplet state. Such quenching would be expected to prevent all photodynamic reactions. Since the reactive oxygen species are very short lived they react only with substrates in their immediate vicinity. Thus, only sensitizer bound to viral particles or RBC can be involved in producing photodynamic damage. Several hypotheses, which are not mutually exclusive, to explain our findings are possible. One is that Trolox™ can interact with phthalocyanines that are bound to RBC but not with those bound to VSV, thus affording protection for the former only. It is unlikely that quenching of the phthalocyanine triplet state by Trolox™ is the major protective mechanism, since the rate constant for quenching the triplet state of AlPcS$_4$ by oxygen is $1.7 \times 10^9 M^1s^1$, two orders of magnitude higher. See I. Rosenthal et al, *Photochem. Photobiol.*, 60:215–220 (1994). However, bult Trolox™ concentration, 5 mM, is 20-fold higher than that of oxygen for air-saturated solution, and its local concentration at the reaction site may be lower or higher.

Another possibility is that quenching of reactive oxygen species, whether type I or type II, by Trolox™ is effective only at the RBC membrane but not at the viral membrane. This could be due to Trolox™ binding much more effectively to the RBC membrane than to virus and/or Trolox™ being more effective in quenching type I photoreactants that are produced in RBC than in quenching singlet oxygen that is the primary mediator of viral damage. In addition, the site at the membrane to which Trolox™ binds could also be critical in explaining its differential protection of RBC versus VSV.

At any rate, it is not our intention to be bound by theory. Whatever the mechanism is by which Trolox™ exerts its selective protection against phthalocyanine-sensitized photodamage, this finding would appear to be of practical importance. By optimizing Trolox™ concentration together with other parameters, such as fluence rate, it is possible to achieve complete sterilization of lipid enveloped viruses in RBC concentrate without significantly compromising RBC structure and function.

It will be appreciated that the instant specification and claims are set forth by way of illustration and not limitation, and that various modifications and changes may be made without departing from the spirit and scope of the present invention.

What is claimed is:

1. A method of reducing K+ leakage from red blood cells in a red blood cell-containing composition during irradiation comprising conducting irradiation of the red blood cell-containing composition in the presence of vitamin E or a derivative thereof.

2. The method of claim 1, wherein the vitamin E or a derivative thereof is selected from the group consisting of α-tocopherol phosphate, α-tocopherol succinate and 6-hydroxy-2,5,7,8-tetramethylchroman-2-carboxylic acid (Trolox).

3. The method of claim 1, wherein the vitamin E derivative is 6-hydroxy-2,5,7,8-tetramethyl-chroman-2-carboxylic acid (Trolox).

4. The method of claim 1, wherein the red blood cell composition is blood.

* * * * *